United States Patent [19]

Harris

[11] 4,400,469
[45] Aug. 23, 1983

[54] PRODUCTION OF ETHANOL FROM JERUSALEM ARTICHOKES

[76] Inventor: Fritz B. Harris, 590 Payne Rd., San Juan Bautista, Calif. 95045

[21] Appl. No.: 273,365

[22] Filed: Jun. 15, 1981

[51] Int. Cl.$^3$ ............................ C12P 7/06; A23K 1/00
[52] U.S. Cl. ...................................... 435/161; 426/49; 426/52; 426/60
[58] Field of Search ................... 435/161; 426/49, 52, 426/60, 615, 635

[56] References Cited

U.S. PATENT DOCUMENTS 2,085,003   6/1937   Christensen et al. ............... 435/165

FOREIGN PATENT DOCUMENTS 2809531   9/1978   Fed. Rep. of Germany ........ 426/49
2906977   9/1980   Fed. Rep. of Germany ...... 435/161

OTHER PUBLICATIONS

Winton et al., *The Structure and Composition of Foods*, vol. II, John Wiley & Sons, Inc., N.Y.; ©1935, pp. 171-175.

*Primary Examiner*—Raymond N. Jones
*Assistant Examiner*—Elizabeth J. Curtin
*Attorney, Agent, or Firm*—Paul B. Fihe

[57] ABSTRACT

Disclosed herein is a new method of producing ethanol from the Jerusalem Artichoke (*Helianthus tuberosus*) by removing the sugar juices from the stalk before the sugar moves down into the tubers and directly fermenting the sugar to produce ethanol, thereby eliminating the necessity of converting the resulting starches found in the tubes to fermentable sugars before fermenting the sugar to produce ethanol. The method must be very accurately carried out to make use of the maximum sugar content of the Jerusalem Artichoke as follows: the Jerusalem Artichoke stalk must be cut above the tubers immediately before the plant flowers to retain all of the sugar in the stalk; the stalk is then ground in a hammermill to release the sugars from the central cylinder, the pith, the ligneous cells, and to a small amount from the bark; the sugar juices from the hammermill are collected; the remaining mass of the central cylinder, pith, ligneous cells and bark is squeezed to remove the remaining sugar juices; the entire collected sugar juice is then processed by 1) bringing the pH to 4.0–4.5, 2) heating to 80°–82° F., 3) adding yeast, 4) fermenting for approximately 24 hours, and then 5) distilling to produce ethanol. The method produces the maximum quantity of high grade ethanol per acre of plant of any known plant source, permitting the leaves to be used to return a high nitrogen content of the soil, the ground stalk mass to provide protein as an animal food, and the tubers to provide human or animal foods. The method for the first time uses the entire Jerusalem Artichoke while providing the maximum amount of ethanol as a worldwide energy source by the least costly, least complicated, and most energy efficient process.

8 Claims, 2 Drawing Figures

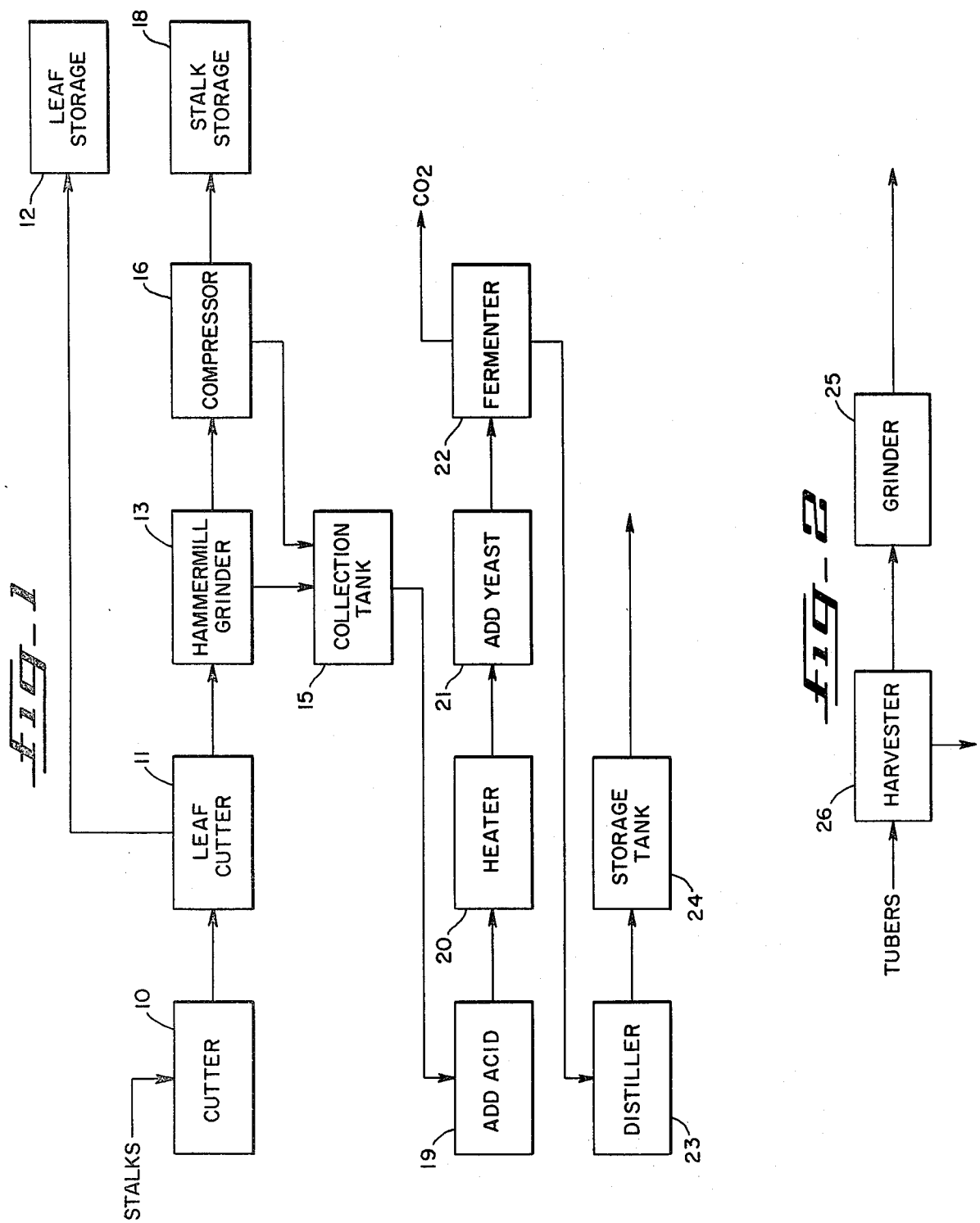

PRODUCTION OF ETHANOL FROM JERUSALEM ARTICHOKES

FIELD OF THE INVENTION

The present invention relates to the production of ethanol, and more particularly to a method of producing ethanol from Jerusalem Artichokes.

BACKGROUND OF THE INVENTION

Although the process for producing ethanol from plants and fruits has been known and used for many years, the large-scale production of ethanol for fuel has been limited by the fact that the plant sources, such as corn and sugarcane, are urgently required for both human and animal consumption. Only the Jerusalem Artichoke, with its high sugar content and its ability to be grown in a wide variety of conditions in great volumes per acre, has been available for large commercial production of ethanol for fuel, free from the basic needs for human and animal consumption. In the past, the existence of the sugar source in the Jerusalem Artichoke tubers has been known; therefore, all processes for making ethanol from the Jerusalem Artichoke involved the use of harvested tubers. This tuber utilization process for commercial production of ethanol on a large scale is severely limited by the excessive time, energy consumption and cost, due to the necessity of first having to break down and convert the tuber starch with enzymes to provide a fermentable sugar, and only after this long process could the sugar then be fermented to produce ethanol. The fact that fermentable sugar in quantity equal to the sugar processed from the tuber was already available in the stalk just before the flowering of the Jerusalem Artichoke has escaped recognition until now, in this method being described herein.

SUMMARY OF THE PRESENT INVENTION

Accordingly, it is the general objective of the present invention to provide a method of ethanol production from the stalks of Jerusalem Artichokes.

The present invention was developed to meet the challenge of energy and food needs and provide a plentiful source of both energy and food from a plant not yet being used on a commercial scale due to prohibitively high time, energy and cost requirements in processing. The Jerusalem Artichoke was selected for this production of energy and food due to first, its very high sugar content; second, its unusual ability to thrive in most climatic conditions including arid areas; and third, its ability to produce tremendous volumes of plants per acre in as many as three crops per year.

Until the present described method, no practical means was known to obtain all of the Jerusalem Artichoke sugar in a fermentable state other than the time and energy inefficient two-stage process of converting the starch in the tubers to fermentable sugar and then fermenting the sugar to produce ethanol. The concept of using the tubers for this complicated, costly process after the sugar goes down into the tuber and must be converted from the resulting starch does not commend itself to logical thinking or commercial practicality. The present invention utilizes all of the sugar from the stalk at its maximum level before the flowering of the plant and before the sugar goes into the tuber. Therefore, no conversion of starch is required to provide fermentable sugar.

Briefly, after the stalk is cut, the leaves are removed and the stalks are then ground so as to release the sugar juices. Preferably, the ground stalks are then compressed to permit extraction of additional sugar juices. The collected sugar juice is then subjected to a fermentation and distillation process to produce the ethanol, it again being notable that no conversion of starch to sugar is required, thus reducing time and cost of ethanol production.

Further objects are to provide for the complete use of the Jerusalem Artichoke plant for not only ethanol, but for nitrogen from the leaves for the soil, protein from the ground stalk mass after the sugar removal for animal food, and harvested tubers for both human and animal food. A portion of the tubers may be left in the ground for the producing of the next crop.

The invention further resides in the combination construction and arrangement of the parts illustrated in the accompanying drawing, and while there is shown therein a preferred embodiment thereof, it is to be understood that the same is illustrative of the invention and that the invention is capable of modification and change, and comprehends other details of construction without departing from the spirit thereof or the scope of the appended claims.

BRIEF DESCRIPTION OF THE DRAWING

The stated objective of the invention and the manner in which it is achieved as summarized hereinabove will be more readily understood by reference to the following detailed description of the exemplary embodiment of the invention shown in the accompanying drawing wherein:

FIG. 1 is a progressive schematic diagram indicating the steps in producing ethanol from Jerusalem Artichoke stalks with by-products of leaves to soil and stalk mass to animal food, FIG. 2 is a schematic illustration of the preparation of Jerusalem Artichoke tubers for human and animal foods.

DETAILED DESCRIPTION OF THE EXEMPLARY EMBODIMENT OF THE INVENTION

Referring now more particularly to FIG. 1, there are shown the successive steps in producing ethanol from the stalks of Jerusalem Artichokes and the utilization of the leaves and stalk ground mass. In FIG. 1 the initial step of the method constitutes the cutting of the stalk just above the tuber, as indicated at 10. This cutting takes place immediately before the Jerusalem Artichoke begins to flower and while the sugar content of the stalk is at a maximum. The cut stalks are then subjected to a leaf removal step 11, where the leaves are cut off and transferred to storage 12 for later return to the soil to replenish the nitrogen content of the soil and to supply additional humus. The stalks are now moved to a hammermill 13 for grinding. This grinding step is to release the sugar juices as much as possible and prepare the stalk central cylinder, the pith, the ligneous cells and the bark for squeezing in the compressor 16 in the next step of the method. The directly released juices from the grinder 13 are then collected in a tank 15. In the compressor 16, a fine screen with $\frac{3}{8}$ inch to $\frac{1}{2}$ inch holes reduced the stalk mass sufficiently to permit a thorough squeezing of the mass to remove all of the remaining sugar juices in the compressor 16, which are then also collected in the storage tank 15. The compressed stalk mass is then transferred to storage 18, to be used as animal food.

The sugar juices now collected in the storage tank 15 are clear of any stalk mass and are now ready to be transferred to the fermentation process. The stalk sugar juices are now fermentable directly in the very simple remaining process. Initially, the sugar juices are brought up to a pH of 4.0–4.5 by adding sulphuric acid 19 prior to fermentation steps. This pH permits the yeast to accomplish its function of producing ethanol from the sugar juices and not acting to increase the acid level by making acid with the sugar juices. The yeast is free to produce only ethanol and $CO_2$ with this pH. The sugar juices are then heated to 80° F.–82° F., as indicated at 20, to provide the optimum condition for the function of the yeast when it is added as the next step 21. Approximately three (3) ounces of distillers yeast is added for every ten (10) gallons of sugar juices. The amount may be varied to alter the time of the yeast action in the fermentation process. The frementing of the mixture is carried out under the conditions of pH 4.0–4.5 and 80° F.–82° F. The fermentation tank 22 is fitted with a lock device which permits the $CO_2$ produced during fermentation to leave the tank. The $CO_2$ may be collected for special use or may be exhausted to the atmosphere harmlessly. The fermentation process will continue for approximately twenty-four (24) hours, depending on the amount of yeast used. The cessation of bubbling in the lock will indicate the completion of fermentation. Then the alcohol vapors captured by the lock and now condensed in the water in the lock may be returned to the fermented liquid for transfer to the distilling unit 23. The liquid from the fermentation process is distilled by normal distilling to produce ethanol of 160 proof, or higher if required. The ethanol is then stored in tanks 24, to be used as a fuel.

Referring now to FIG. 2, the utilization of the Jerusalem Artichoke tubers is schematically represented. With the sugar juices already obtained from the stalks, rather than being allowed to go down into the tubers as occurs normally at the time of the flowering of the plant, the tuber now is principally valuable as a food high in proteins. After harvesting 26, the tubers can then be shredded or ground 25, to produce a food material for animals. The tuber mass from the grinder 25 may be dried or used wet as an animal food. The tubers may also be used in the harvested condition, after cleaning, to be a food for human consumption. Or the tubers may be used as the replanting seed for the next crop of Jerusalem Artichokes. This replanting cycle can be simplified or eliminated by leaving part or all of the tubers in the ground to produce the next crop; usually only a portion of the total tuber population will suffice for the next crop. In any of the cases where some or all tubers are left in the ground, the field may simply be readied for the next crop growth by discing the field to slice up the remaining tubers and forcing them into general row orientation.

In FIG. 1 and FIG. 2, the complete process schematic represents the preferred method for producing ethanol from Jerusalem Artichoke stalks, and the complete utilization of all parts of the plant in the manner which is best suited to using the sugar juices, proteins, nitrogen, and humus to the fullest extent. It will be apparent that many modifications and/or alterations in this method as described can be made without departing from the spirit of the present invention, and accordingly the foregoing description is to be considered as purely exemplary and not in a limiting sense, and the actual scope of the invention is to be indicated only by reference to the appended claims.

What is claimed is:

1. The method of producing ethanol which comprises the steps of
    cutting the stalks of Jerusalem Artichokes above the tubers shortly before flowering,
    grinding the cut stalks to release the sugar juices therefrom,
    fermenting the sugar juices, and
    distilling the fermented liquid.
2. The method of producing ethanol according to claim 1 which comprises the additional step of
    compressing the ground stalk mass to effect additional release of sugar juices.
3. The method of producing ethanol according to claim 1 which comprises
    adding acid to the released sugar juices to bring the pH of 4.0 to 4.5 prior to fermentation.
4. The method of producing ethanol according to claim 3 wherein
    the added acid is sulphuric.
5. The method of producing ethanol according to claim 1 which comprises
    the additional step of removing the leaves from the stalks prior to the grinding step.
6. The method of producing ethanol according to claim 5 wherein the fermentation step includes
    heating the juices to 80° F.–82° F., and
    adding yeast in an appropriate amount for fermentation.
7. The method of producing ethanol according to claim 5 which comprises
    separate harvesting and utilization of the tubers for food or replanting.
8. The method of producing ethanol from Jerusalem Artichokes and utilizing all parts of the said plant which includes the steps of
    cutting the stalks just above the tubers shortly before flowering,
    removing the leaves for return to the soil or other use,
    grinding the stalks with a hammermill to release the sugar juices found in the central cylinder, the pith, the ligneous cells and in the bark,
    then compressing the stalk mass to remove all the sugar juices therefrom,
    collecting all the sugar juices for fermentation,
    storing the stalk mass now free of sugar juices for using as animal food, dried or wet,
    then fermenting the sugar juices after first bringing the pH to 4.0–4.5 by adding sulphuric acid,
    heating to 80° F.–82° F.,
    adding the required yeast,
    removing the $CO_2$ during fermentation,
    fermenting for approximately 24 hours,
    distilling the liquid remaining after the completion of fermentation to obtain 160 proof or higher ethanol to be used as fuel, and
    then utilizing the tubers for human food or replanting.

* * * * *